US00PP25356P3

(12) United States Plant Patent
Hammett

(10) Patent No.: US PP25,356 P3
(45) Date of Patent: Mar. 17, 2015

(54) ***DAHLIA* PLANT NAMED 'MYSTIC MEMORIES'**

(50) Latin Name: *Dahlia variabilis*
Varietal Denomination: Mystic Memories

(71) Applicant: Keith Hammett, Auckland (NZ)

(72) Inventor: Keith Hammett, Auckland (NZ)

( * ) Notice: Subject to any disclaimer, the term of this patent is extended or adjusted under 35 U.S.C. 154(b) by 135 days.

(21) Appl. No.: 13/986,664

(22) Filed: May 22, 2013

(65) Prior Publication Data

US 2013/0326782 P1 Dec. 5, 2013

Related U.S. Application Data

(60) Provisional application No. 61/689,283, filed on May 31, 2012.

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Annette Para
(74) *Attorney, Agent, or Firm* — Barbara Campbell; Cochran Freund & Young LLC

(57) ABSTRACT

A new cultivar of *Dahlia* plant named 'Mystic Memories' that is distinguishable by glossy mahogany-black divided leaves, dark purple-brown stems and flowers which are soft peach in color, bearing orange-red highlights and orange-red eye around a dark central disc, is disclosed.

2 Drawing Sheets

Figure 1:
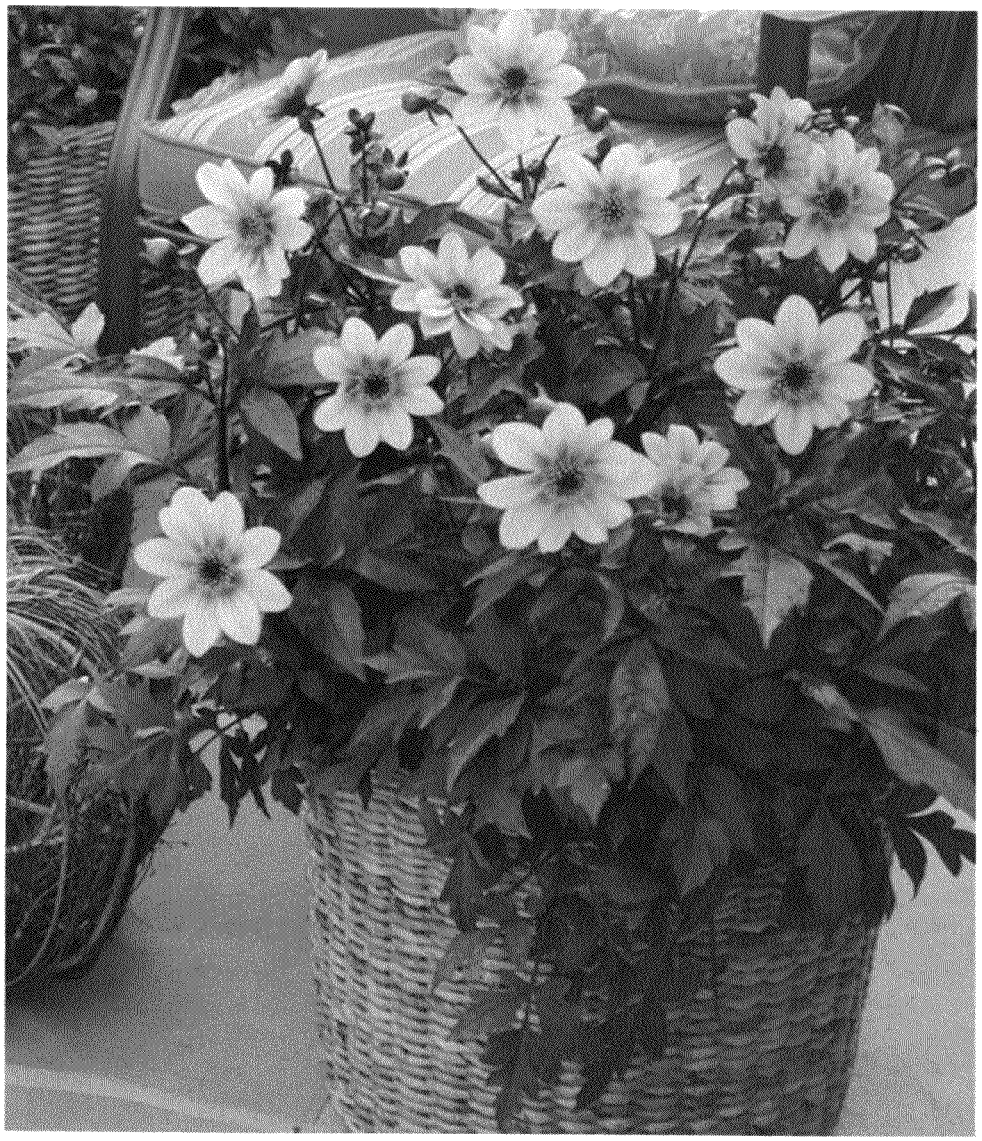

Genus and species: *Dahlia variabilis.*
Variety denomination: 'Mystic Memories'.

BACKGROUND OF THE NEW PLANT

The present invention relates to a new and distinct cultivar of *dahlia* grown for use in mixed combinations, beds and the landscape. The new invention is known botanically as *Dahlia variabilis* and will be referred to hereinafter by the cultivar name 'Mystic Memories'. This application is co-pending with the application Ser. No. 13/986,663 for the inventor's variety of *Dahlia* plant named 'Mystic Fantasy'.

The specific epithet *variabilis* represents a hybrid seedling line that came from crossing various original wild species in the early 1800's, and refers to the species' wide range of flower color and shapes. *Dahlia* is in the family Compositae. The flower of 'Mystic Memories' is a "single" form blossom and exhibits a single row of ray flowers surrounding a central cluster of disc florets.

'Mystic Memories' was selected as a seedling that resulted from the controlled cross-pollination carried out by the inventor in a cultivated area of Auckland, New Zealand in 2007. The inventor selected as female parent an individual plant of *Dahlia variabilis* known by code number '71509/01' which is an unreleased seedling from the inventor's breeding program. The chosen male parent was the inventor's variety *Dahlia variabilis* 'Zone Ten' (U.S. Plant Pat. No. 19,885). Seed was collected from the female parent and sown with the intention of making a selection from the seedlings that resulted.

'Mystic Memories' was selected in 2008 based on the criteria of leaf color, leaf shape, plant height, self-supporting plants, single blooms and flower color. The unique traits that distinguish 'Mystic Memories' from other varieties of *Dahlia* known to the inventor are glossy mahogany-black divided leaves and profusions of soft peach blooms with orange-red highlights and orange-red eye around a dark central disc.

The first asexual reproduction of 'Mystic Memories' was conducted in 2008 in Auckland, New Zealand. The method of asexual propagation utilized was softwood cuttings taken from the first year tuber. Since that time under careful observation, the distinguishing characteristics have been determined stable, uniform, and to be reproduced true to type in subsequent generations of asexual propagation.

SUMMARY

The following traits have been repeatedly observed and represent the distinguishing characteristics of the new *Dahlia* cultivar named 'Mystic Memories'. These traits in combination distinguish 'Mystic Memories' from all other existing varieties of *Dahlia* known to the inventor. 'Mystic Memories' has not been tested under all possible conditions and phenotypic differences may be observed with variations in environmental, climatic, and cultural conditions, however, without any variance in genotype.

1. 'Mystic Memories' exhibits compact rounded habit.
2. 'Mystic Memories' exhibits glossy mahogany-black divided leaves and dark purple-brown stems.
3. 'Mystic Memories' is grown for use in mixed combinations, beds and the landscape.
4. 'Mystic Memories' exhibits soft peach blooms with orange-red highlights and orange-red eye around a dark central disc.
5. 'Mystic Memories' blooms from summer until fall.
6. 'Mystic Memories' grows to 80.0 cm in height and 60.0 cm in width at maturity
7. 'Mystic Memories' is hardy to USDA Zone 9.

COMPARISON WITH PARENTAL AND KNOWN VARIETY

The new *Dahlia* named 'Mystic Memories' is distinguishable from the parents predominantly by flower color. The flowers of each of the parents exhibit mauve radial stripes and pale lavender margins, while 'Mystic Memories' has soft peach blooms with orange-red highlights and orange-red eye around a dark central disc.

The variety of *Dahlia* which is considered by the inventor to most closely resemble 'Mystic Memories' is *Dahlia* 'Mystic Fantasy' (U.S. Plant Patent Application pending). 'Mystic Memories' has soft peach blooms with orange-red highlights and orange-red eye around a dark central disc, while the flowers of 'Mystic Fantasy' are flamingo pink with a soft yellow halo.

DESCRIPTION OF THE PHOTOGRAPHS

Figure 2:
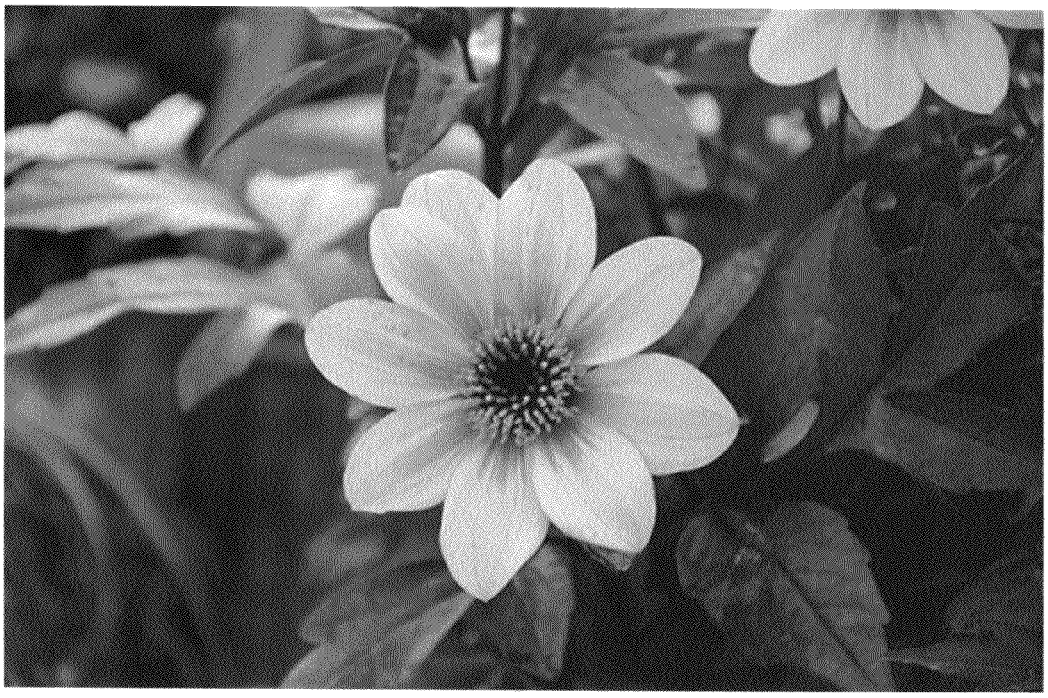

The accompanying color photographs labeled FIG. 1 and FIG. 2 illustrate the overall appearance of the new *Dahlia* cultivar named 'Mystic Memories' showing the colors as true as is reasonably possible to obtain in colored reproductions of this type. Colors in the photographs may differ from the color values cited in the detailed botanical description, which accurately describes the actual colors of the new *Dahlia* variety named 'Mystic Memories'. The photographs were made from digital photographs of four months old from a cutting plant grown outdoors in Santa Barbara, Calif.

FIG. 1 depicts the entire plant in bloom and demonstrates that the foliage of 'Mystic Memories' is consistently mahogany-black when grown in full sun. Any part of the plant which is in shade, including the shade of other plant parts, turns to olive green in color. This coloration is reversible such that the olive-green foliage returns to mahogany-black when exposed or re-exposed to full sun.

FIG. 2 depicts a close-up view of a flower of 'Mystic Memories'.

DESCRIPTION OF THE NEW VARIETY

The following is a detailed botanical description of the new *Dahlia* cultivar named 'Mystic Memories'. Observations, measurements, values and comparisons were collected in Santa Barbara, Calif. from 2-liter container four month old plants. Color determinations were made in accordance with The 2007 Royal Horticultural Society Colour Chart from London England, except where general color terms of ordinary dictionary significance are used. Growing requirements are similar to the species.

Classification:
- *Botanical classification.*—*Dahlia variabilis.*
- *Family.*—Compositae.
- *Denomination.*—'Mystic Memories'.
- *Common name.*—*Dahlia.*

Parentage: *Dahlia variabilis* 'Mystic Memories' is a seedling selection made from plants grown from seed which resulted from the cross-pollination of the following parents:
- *Female parent.*—*Dahlia variabilis* code number '71509/01' (unreleased and unpatented).
- *Male parent.*—*Dahlia variabilis* 'Zone Ten' (U.S. Plant Pat. No. 19,885).

Plant:
- *Propagation method.*—Tissue culture, cuttings, tubers.
- *Rooting system.*—Fine and fibrous.
- *Vigor.*—Vigorous.
- *Habit.*—Upright habit.
- *Use.*—For use in mixed combinations, beds and the landscape.
- *Type.*—Perennial.
- *Dimensions.*—80.0 cm in height and 60.0 cm in width.
- *Cultural requirements.*—Grow in full sun with regular water, and well-draining potting soil.
- *Pest susceptibility.*—Susceptible to aphids.
- *Disease susceptibility.*—Susceptible to mildew in highly humid conditions.
- *Hardiness.*—USDA Zone 9.

Stems:
- *Color.*—RHS N186B.
- *Dimensions.*—45.0 cm in length and 0.4 cm in width.
- *Shape.*—Cylindrical.
- *Surface.*—Glabrous.
- *Internode length* (*average*).—7.0 cm.

Leaves:
- *Type.*—Evergreen.
- *Leaf arrangement.*—Opposite.
- *Leaf division.*—Simple.
- *Leaf dimensions* (*average*).—11.50 cm in length and 9.0 cm in width.
- *Leaf color* (*adaxial surface*).—RHS N186A.
- *Leaf color* (*abaxial surface*).—RHS 189A.
- *Margin.*—Ciliate and pinnatisect.
- *Leaf shape.*—Hastate.
- *Leaf base.*—Attenuate.
- *Leaf apex.*—Apiculate.
- *Leaf venation pattern.*—Pinnate.
- *Vein color* (*abaxial and adaxial surfaces*).—RHS N186C.
- *Leaf surfaces* (*abaxial surfaces*).—Slightly puberulent.
- *Leaf surfaces* (*adaxial surfaces*).—Glabrous.
- *Leaf attachment.*—Petiolate.
- *Petiole shape.*—Sulcate.
- *Petiole dimensions.*—2.50 cm to 4.0 cm in length and 0.10 cm in width.
- *Petiole color.*—RHS N186B.
- *Presence of stipules or spines.*—None observed.

Inflorescence:
- *Inflorescence type.*—Capitulum; flowers classified as "single" form, with single row of ray flowers surrounding a central cluster of disc florets.
- *Aspect.*—Facing upward and outward.
- *Inflorescence quantity per plant.*—15 to 20 per 2-liter container plant.
- *Dimensions of inflorescence* (*average*).—8.0 cm in diameter and 6.0 cm in depth.
- *Inflorescence shape.*—Radiate with center disc.
- *Blooming seasons.*—Summer and fall.
- *Self-cleaning or persistent.*—Self-cleaning.
- *Fragrance of inflorescence.*—Perfumed.

Peduncle:
- *Dimensions* (*average*).—10.0 cm in length and 0.40 cm in diameter.
- *Shape.*—Cylindrical.
- *Surface.*—Glabrous.
- *Color.*—RHS N186B.

Bud:
- *Shape.*—Oblate.
- *Dimensions* (*average*).—2.0 cm in height and 1.75 cm in diameter.
- *Surface.*—Glabrous.
- *Appearance.*—Semi-glossy.
- *Color.*—RHS 187A.
- *Apex.*—Obtuse.
- *Base.*—Truncate.

Ray florets:

*Quantity per inflorescence.*—8 or 9.

*Dimensions* (*average*).—4.50 cm in length and 2.50 cm in width.

*Form.*—Petaloid.

*Shape.*—Obovate.

*Surface* (*adaxial and abaxial*).—Glabrous.

*Arrangement.*—Radiate.

*Apex.*—Obtuse.

*Base.*—Cuneate.

*Margin.*—Entire.

*Color* (*adaxial and abaxial surfaces*).—Predominantly RHS 29B becoming RHS 42C towards and at base; typically two pale yellow longitudinal stripes RHS 9D.

*Vein.*—Fine, parallel, color RHS 42C.

Disc florets:

*Disc diameter.*—1.5 cm to 2.0 cm.

*Quantity of disc florets.*—In excess of 90 per inflorescence.

*Disc floret dimensions.*—1.75 cm in length and 0.10 cm in width.

*Disc floret color.*—RHS 187A.

*Petals.*—8 in number.

*Petals fused or unfused.*—Fused.

*Petal apex.*—Acute.

*Petal surface* (*ventral and dorsal surfaces*).—Glabrous.

*Receptacle dimensions.*—1.0 cm in depth and 1.60 cm in diameter.

*Receptacle surface.*—Glabrous.

*Receptacle color.*—RHS 187A.

Phyllary:

*Inner phyllary.*—Number: 8. Shape: Elongated ovate. Dimensions: 2.50 cm in length and 0.7 cm in width. Color (adaxial and abaxial surfaces): Between RHS N199B and RHS N199C. Texture: Scarious. Appearance: Translucent. Apex: Subacute. Base: Truncate. Margin: Entire. Surface (adaxial and abaxial): Glabrous.

*Outer phyllary.*—Number: 5 in number. Shape: Obovate. Dimensions: 1.50 cm in length and 0.75 cm in width. Color (adaxial and abaxial surfaces): RHS N187A and RHS N189A both present. Form: Reflexed. Apex: Obtuse. Base: Truncate. Margin: Entire. Surface (adaxial and abaxial): Glabrous.

Reproductive organs:

*Stamens.*—5 in number.

*Stamen attachment*.—Filament adnate to ventral surface of corolla.

*Stamen length.*—6.0 mm in length.

*Stamen color*.—RHS 166A.

*Anther*.—Connate.

*Anther color*.—RHS 166A.

*Pollen*.—Present.

*Quantity*.—Large amount.

*Pollen color*.—RHS N163D.

*Pistil*.—One present.

*Pistil length.*—9.0 mm in length.

*Stigma dimensions.*—3.0 mm in length and 4.50 mm in width.

*Stigma form*.—Plumose.

*Stigma color*.—RHS N163A.

*Stigma shape*.—Bifurcate.

*Ovary position*.—Inferior.

*Ovary color*.—RHS 150D.

*Ovary shape*.—Rotund.

*Ovary dimensions.*—2.0 mm in width and 3.0 mm in height.

Seed: None observed to date.

I claim:

1. A new and distinct cultivar of *Dahlia* plant named 'Mystic Memories' as described and illustrated herein.

* * * * *